(12) United States Patent
Pinchuk et al.

(10) Patent No.: US 9,731,051 B2
(45) Date of Patent: Aug. 15, 2017

(54) PACEMAKER LEAD AND OTHER MEDICAL IMPLANT DEVICES

(71) Applicant: Innovia LLC, Miami, FL (US)

(72) Inventors: Leonard Pinchuk, Miami, FL (US); Yongmoon Kwon, Weston, FL (US)

(73) Assignee: Innovia LLC, Miami, FL (US)

( * ) Notice: Subject to any disclaimer, the term of this patent is extended or adjusted under 35 U.S.C. 154(b) by 752 days.

(21) Appl. No.: 14/226,087

(22) Filed: Mar. 26, 2014

(65) Prior Publication Data
US 2014/0296679 A1 Oct. 2, 2014

Related U.S. Application Data

(60) Provisional application No. 61/805,311, filed on Mar. 26, 2013.

(51) Int. Cl.
*A61B 5/042* (2006.01)
*A61N 1/05* (2006.01)
(Continued)

(52) U.S. Cl.
CPC ............ *A61L 31/041* (2013.01); *A61B 5/686* (2013.01); *A61L 27/16* (2013.01); *A61N 1/0488* (2013.01);
(Continued)

(58) Field of Classification Search
CPC ....... A61B 5/0408; A61B 5/042; A61B 5/686; A61B 5/6869; A61B 2562/187;
(Continued)

(56) References Cited

U.S. PATENT DOCUMENTS

| 4,484,586 A | 11/1984 | McMickle et al. |
| 5,545,203 A | 8/1996 | Doan |
| (Continued) | | |

OTHER PUBLICATIONS

Vincentz "Benefits of Incompatibility (part 2)" in European Coatings Journal (Sep. 2008).*
(Continued)

*Primary Examiner* — Lee S Cohen
*Assistant Examiner* — Erin M Cardinal
(74) *Attorney, Agent, or Firm* — Gordon & Jacobson, P.C.

(57) ABSTRACT

An implantable medical device for electrical stimulation or sensing includes a body supporting at least one flexible elongate conductor element. The body includes an insulating structure that protects the flexible conductor element(s). The insulating structure is realized from multiple polymer layers wherein at least one of the polymer layers is formed from a polymer blend of a thermoplastic polyurethane material and an isobutylene block copolymer. In one particular embodiment, the insulating structure of the body includes at least a first polymer layer, a second polymer layer and a third polymer layer, where the second polymer layer covers and interfaces to the first polymer layer, and the third polymer layer covers and interfaces to the second polymer layer. The first polymer layer is formed from a thermoplastic polyurethane material. The third polymer layer is formed from an isobutylene block copolymer. The intermediate second polymer layer is compatible with the particular polymers of the first and third polymer layers and is formed from a polymer blend of a thermoplastic polyurethane material and an isobutylene block copolymer.

17 Claims, 3 Drawing Sheets

(51) Int. Cl.
- *A61L 31/04* (2006.01)
- *A61B 5/00* (2006.01)
- *A61N 1/04* (2006.01)
- *A61L 27/16* (2006.01)
- *A61N 1/36* (2006.01)
- *C08L 75/04* (2006.01)

(52) U.S. Cl.
CPC ......... *A61B 5/042* (2013.01); *A61B 2562/222* (2013.01); *A61N 1/05* (2013.01); *A61N 1/36017* (2013.01); *C08L 75/04* (2013.01)

(58) Field of Classification Search
CPC ........ A61B 2562/222; A61B 2562/227; A61N 1/05; A61N 1/056; A61N 1/0587; A61N 1/0595; A61N 1/36017; A61N 1/0488; A61L 31/041; A61L 27/16; C08L 75/04
See application file for complete search history.

(56) References Cited

U.S. PATENT DOCUMENTS

| | | |
|---|---|---|
| 5,584,873 A | 12/1996 | Shoberg et al. |
| 7,555,349 B2* | 6/2009 | Wessman ............ A61N 1/0551 607/116 |
| 8,155,759 B2* | 4/2012 | Pinchuk ................ A61B 5/042 607/119 |
| 2003/0054090 A1 | 3/2003 | Hansen |
| 2003/0087024 A1 | 5/2003 | Flanagan |
| 2005/0234388 A1* | 10/2005 | Amos ................. A61M 27/008 604/8 |
| 2006/0147492 A1 | 7/2006 | Hunter et al. |
| 2007/0162103 A1 | 7/2007 | Case et al. |
| 2010/0076538 A1 | 3/2010 | Desai et al. |
| 2010/0241208 A1* | 9/2010 | Pinchuk ................ A61B 5/042 607/119 |
| 2010/0256720 A1 | 10/2010 | Overstreet et al. |
| 2011/0224019 A1* | 9/2011 | Tutmark ............ A63B 37/0003 473/371 |
| 2011/0288628 A1 | 11/2011 | Noessner et al. |
| 2012/0271385 A1 | 10/2012 | Li et al. |
| 2016/0120986 A1* | 5/2016 | Anderson ............ A61K 31/343 424/443 |

OTHER PUBLICATIONS

"Medical applications of poly(styrene-block-isobutylene-block-styrene) ("SIBS")," Pinchuk et al., Biomaterials (2007), doi:10.1016/j.biomaterials.2007.09.041.

* cited by examiner

PACEMAKER LEAD AND OTHER MEDICAL IMPLANT DEVICES

CROSS-REFERENCE TO RELATED APPLICATION(S)

The present application claims priority from U.S. Provisional Pat. Appl. No. 61/805,311, filed on Mar. 26, 2013, herein incorporated by reference in its entirety.

BACKGROUND

1. Field

The present application relates broadly to medical implant devices and in particular to electrical leads for electrical stimulation or electrical sensing of body organs or tissues (such as implantable cardiac leads for delivering electrical stimulation to the heart) and their method of fabrication.

2. Related Art

Implantable medical electrical stimulation and/or sensing leads (referred to herein as "pacemaker leads" or "lead(s)") are well known in the fields of cardiac stimulation and monitoring, including cardiac pacing and cardioversion/defibrillation. In these applications, a pacemaker or cardioverter/defibrillator implantable pulse generator (IPG) or a cardiac monitor is coupled to the heart through one or more of such leads. The proximal end of such leads is formed with a connector element which connects to a terminal of the IPG or cardiac monitor. The distal end of such leads includes a distal stimulation and/or sensing electrode that is fixated to tissue at the desired treatment site. A lead body extends between the distal and proximal ends. The lead body comprises one or more electrical conductors surrounded by an insulating outer sleeve. Each electrical conductor provides an electrical signal path between the proximal connector element (and the IPG or cardiac monitor coupled thereto) and the distal stimulation and/or sensing electrode. A lead having a single distal stimulation and/or sensing electrode is typically referred to as a unipolar lead. A lead having two or more distal stimulation and/or sensing electrodes is typically referred to as a bipolar (or a multi-polar) lead. The leads are typically implanted using an endocardial approach or an epicardial approach. The endocardial approach is the most common method. The epicardial approach is a less common method in adults, but more common in children.

In the endocardial approach, a local anesthetic is typically applied to numb an incision area of the chest (typically adjacent the collar bone) where one or more leads and the IPG or cardiac monitor are inserted. Each lead is inserted through the incision and into a vein, then guided through a transvenous pathway to the heart with the aid of fluoroscopy. The distal lead electrode is affixed to the heart muscle at the desired treatment site. The proximal connector element of the lead is coupled to the IPG or cardiac monitor, and the IPG or cardiac monitor is placed in a pocket created under the skin in the upper chest. The transvenous pathway can include a number of twists and turns, and the lead body can be forced against bony structures of the body that apply stress to it.

The epicardial approach requires open heart surgery wherein the distal lead electrode of one or more leads is affixed directly to the heart tissue at the desired treatment site, instead of inserting the lead(s) through a vein. The proximal connector element of the lead is coupled to the IPG or cardiac monitor, and the IPG or cardiac monitor is placed in a pocket created under the skin in the abdomen.

In all applications, the heart beats approximately 100,000 times per day or over 30 million times a year, and each beat stresses at least the distal portion of the lead body. The lead conductors and insulation are subjected to cumulative mechanical stresses, as well as material reactions as described below, that can result in degradation of the insulation or fractures of the lead conductors with untoward effects on device performance and patient well being.

In order to facilitate advancement through the transvenous pathway (for the endocardial approach) and minimize stress on the lead body (for all applications), flexible lead bodies have been developed using smaller diameter coiled wire conductors and flexible insulating materials, most notably polyurethane compositions. However, problems have been encountered as to the bio-stability of such lead materials. More particularly, it is acknowledged that there are a number of mechanisms for degradation of elastomeric polyurethane insulation of the lead body in vivo. One is environmental stress cracking (ESC), which is the generation of crazes or cracks in the polyurethane elastomer produced by the combined interaction of a medium capable of acting on the elastomer and a stress level above a specific threshold. Another is metal ion induced oxidation (MIO) in which polyurethane elastomers exhibit accelerated degradation from metal ions such as cobalt ions, chromium ions, molybdenium ions and the like which are used alone or in alloys in the conductive wire of the lead body.

The degradation mechanism of polyether urethanes was elucidated by Anderson's group at Case Western Reserve University (Cleveland, Ohio). They found that the carbon alpha to the ether of the polyether soft segment was oxidized to ester either by superoxide ($O_3$) produced by polymorphonuclear leucocytes (PMNs) and the like, or by metal ion contact of the polyurethane, as occurs on the inside of pacemaker lead insulators. Subsequent hydrolysis of the ester cleaves the macromolecule, and in the presence of flexion, cracks develop. Realizing that the ether groups were vulnerable, the inventor of the subject application introduced more biostable polycarbonate urethanes for implant applications, which were initially commercialized under the trade name Corethane™ by Corvita Corp. of Miami, Fla. and now commercialized under the name Bionate® by DSM PTG of Berkley, Calif.

The improved biostability of polycarbonate urethanes was confirmed by Stoke's group at Medtronic using the "Stokes Test", in which a tube of the material is stretched over a dumbbell-shaped mandrel and exposed to oxidizing and hydrolyzing chemicals, or is implanted in the body for a predetermined time. Materials that are readily susceptible to oxidation and hydrolysis crack in this model; significantly, the polycarbonate urethanes did not crack over the duration tested.

Although polycarbonate urethanes demonstrated superior biostability relative to polyether and polyester urethanes, they too eventually exhibited biodegradation as manifested by surface cracking. The fractures were most noticeable in areas with large numbers of macrophages on histology. Importantly, Wilson's group (The Hospital for Sick Children, Toronto, Ontario) also observed that these degrading implants attracted a plethora of polymorphonuclear leukocytes, especially during the early weeks of implantation. Further, the cleaner the polycarbonate urethane (less extractables, washed surfaces), the more intense the inflammation. Further observations were the attraction of macrophages, foreign body giant cells and the phagocytosis of small "chunks" of polyurethane. Lastly, it was also observed upon careful examination that crack formation in microfilamentous grafts as early as 1 month after implantation. A summary of these finding was recorded in the article by Pinchuk et al., entitled "Medical applications of poly(styrene-block-isobutylene-block-styrene) ("SIBS")," Biomaterials (2007), doi:10.1016/j.biomaterials.2007.09.041. In summary, polyurethanes exhibit degradation with time with signs of the problem occurring within weeks of implantation. Degradation is due to oxidation, most likely by superoxide produced by phagocytes ("scavenger cells"); the more degradation, the greater number of scavenger cells that migrate to the site, the worse the degradation. The more oxygen that can penetrate the polyurethane, the more it degrades and similarly, the more water that absorbs into the polyurethane, the better the transport of oxygen and other substances, for example, hydrogen ion, that can degrade the polymer.

SUMMARY

It is therefore an object of the present disclosure to provide an implantable medical device for electrical stimulation or sensing with an insulator having improved resistance to in vivo degradation.

It is another object of the present disclosure to provide an implantable medical device for electrical stimulation or sensing having excellent flexibility and mechanical properties.

In accord with one embodiment of the present disclosure, an implantable medical device for electrical stimulation or sensing includes a body supporting at least one flexible elongate conductor element. The body can include a proximal connector element and a distal electrode, and the elongate conductor element can provide an electrical signal path between the proximal connector element and the distal electrode. The body includes an insulating structure that protects the flexible conductor element(s). The insulating structure is realized from multiple polymer layers wherein at least one of the polymer layers is formed from a polymer blend of a thermoplastic polyurethane material and an isobutylene block copolymer.

The multiple polymer layers of the insulating structure can include an outer coating layer that covers a polymer layer formed from the polymer blend. In one embodiment, the outer polymer coating layer is formed from an isobutylene block copolymer which preferably has a polyisobutylene block and a polystyrene block.

The insulating structure can encapsulate the elongate conductor element(s) of the body. The elongate conductor element(s) can include a coiled wire conductor defining a central axis with an outer surface facing radially outward away from the central axis and an inner surface facing radially inward toward the central axis.

In one embodiment, the insulating structure of the body includes at least a first polymer layer, a second polymer layer and a third polymer layer, where the second polymer layer covers and interfaces to the first polymer layer, and the third polymer layer covers and interfaces to the second polymer layer. The first polymer layer is formed from a thermoplastic polyurethane material. The third polymer layer is formed from an isobutylene block copolymer. The intermediate second polymer layer is compatible with the particular polymers of the first and third polymer layers and is formed from a polymer blend of a thermoplastic polyurethane material and an isobutylene block copolymer. For example, the intermediate second polymer layer is configured to readily bond to both the first and second polymer layers while avoiding interfacial delamination and disbonding over time.

The third polymer layer can be an outer coating layer that covers the second polymer layer. The isobutylene block copolymer of the third layer and the polymer blend of the second layer can have a polyisobutylene block and a polystyrene block.

The polymer blend of the thermoplastic polyurethane material and the isobutylene block copolymer can be mixed in a melt or in a solution as described herein.

The polymeric materials of the implantable medical devices as described herein can be used for other medical implant applications, such as for an artificial disk for the spine, a dynamic stabilizer for the spine, an artificial tendon, an artificial ligament, an indwelling catheter, a drug delivery device, a hernia mesh, a heart valve, or other implantable medical device.

Additional objects and advantages of the present disclosure will become apparent to those skilled in the art upon reference to the detailed description taken in conjunction with the provided figures.

DETAILED DESCRIPTION OF THE PREFERRED EMBODIMENTS

As is well known, a "polymer" is a substance that has a molecular structure that includes a large number of one or more constitutional units (commonly referred to as monomers) that are bonded to one another. As used herein, the term "monomer" may refer to free monomers and to those that have been incorporated into polymers, with the distinction being clear from the context in which the term is used.

Polymers may take on a number of configurations, which may be selected, for example, from linear, cyclic and branched configurations, among others. Branched configurations include star-shaped configurations (e.g., configurations in which three or more chains emanate from a single branch point), comb configurations (e.g., configurations having a main chain and a plurality of side chains, also referred to as "graft" configurations), dendritic configurations, and so forth.

As used herein, a "copolymer" is a polymer consisting of at two dissimilar constitutional units.

As used herein, "block copolymers" are copolymers that contain two or more polymer blocks that differ in composition, for instance, because a constitutional unit (i.e., a monomer or homopolymer) is found in one polymer block that is not found in another polymer block. As used herein, a "polymer block" or "block" is a grouping of constitutional units. Blocks can be unbranched or branched.

As used herein, a "polymer blend" is a material derived by mixing together or blending at least two different polymers; the mixing of the polymers can be carried out in a melt or in a solution.

Figure 1A:
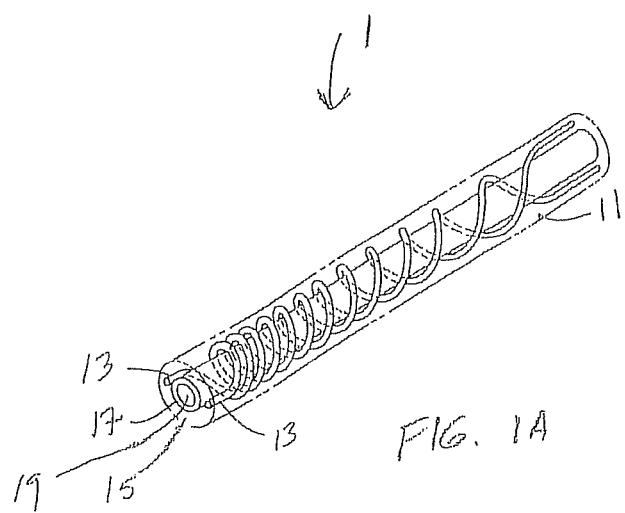
FIG. 1A is a perspective view of the body of an implantable pacemaker lead in accordance with an embodiment of the present application.
Figure 1B:
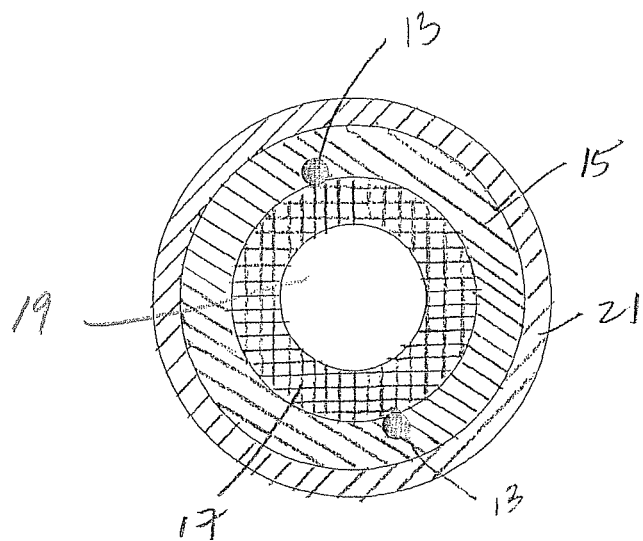
FIG. 1B is a cross-sectional view of the pacemaker lead body embodiment of FIG. 1A.

Turning now to FIGS. 1A and 1B, a flexible pacemaker lead 1 is provided with a lead body 11 that includes one or more flexible conductor elements 13 surrounded by a coaxial insulating structure. The coaxial insulting structure includes an outer insulating part 15 and an inner insulating part 17 with the coiled wire conductors 13 encapsulated between the outer insulating part 15 and inner insulating part 17 as shown in FIG. 1B. In the illustrative embodiment shown, the flexible conductor element 13 includes two coiled wire conductors. Each coiled wire conductor can be made of a metal or other suitable conductive material. The conductive material can be coated with a layer of insulating material. Each coiled wire conductor defines a central axis with an outer surface facing radially outward away from the central axis and an inner surface facing radially inward toward the central axis. The outer insulating part 15 encapsulates and insulates the coiled wire conductors 13 along the length of the lead body. In this configuration, the outer insulating part 15 surrounds the outer surface of the coiled wire conductors and the inner insulating part 17 surrounds the inner surface of the coiled wire conductors.

In the preferred embodiment, the inner insulating part 17 defines a guide channel lumen 19 that removably receives a stylet or guide wire that aids in maneuvering the lead body during implantation as is well known. The proximal end of lead body 11 includes a connector element (not shown) which connects to a terminal of the IPG or cardiac monitor. The distal end of the lead body 11 includes at least one distal stimulation and/or sensing electrode (not shown) that is fixated to cardiac tissue at the desired treatment site. The conductor element(s) 13 provide an electrical signal path between the proximal connector element (and the IPG or cardiac monitor coupled thereto) and the distal stimulation and/or sensing electrode(s).

The outer insulating part 15 and preferably the inner insulating part 17 are both realized from a polymer blend of a thermoplastic polyurethane material and an isobutylene block copolymer. The thermoplastic polyurethane material of the polymer blend can be any type of polyurethane; e.g., any polyurethane with soft segments generally described as polyesters, polyethers, aliphatics, polycarbonates and mixtures thereof. The soft segments can be macrodiols terminated with diols, triols or multiols. In addition they can be macroamines terminated with diamines, triamines and multiamines and combinations thereof and in combination with diols. The thermoplastic polyurethane material of the polymer blend can include an isocyanate component, which can be diisocyanates such as methylene bisphenyldiisocyanate (MDI), hydrogenated methylenebisphenyl diisocyanage (HMDI), toluene diisocyanate (TDI) hexamethylene dissocyanate, isophorone diisocyanate, and the like. The thermoplastic polyurethane material of the blend can also include chain extenders, which can be 1,4-butanediol, ethylene glycol, ethylene diamine, 1,6-hexandiol, etc. The resultant polyurethane or polyureas is the reaction product of a soft segment with a dissocyanate and with a chain extender (or it need not use a chain extender). The synthesis of such thermoplastic polyurethane material of the polymer blend is generally well-known in the art. In one embodiment, the thermoplastic polyurethane material of the polymer blend is a polyetherurethane, such as Pellethane® 80A sold commercially by the Lubrizol Corporation of Wickliffe, Ohio.

The isobutylene block copolymer of the polymer blend is a block copolymer that includes, at least in part thereof, a block derived from isobutylene. The isobutylene block copolymer of the polymer blend can be constituted by a block derived from isobutylene (which can be referred to as block component (a)) and a block derived from a monomer component other than isobutylene (which can be referred to as block component (a)). The block component (a) can include polyisobutylene. In this manner, the isobutylene block copolymer of the polymer blend can include polyisobutylene blocks. The block component (a) may contain (or may not contain) monomer or homopolymer parts derived from another monomer other than isobutylene. The block component (b) is not particularly restricted, and can be derived from a cation-polymerizable monomer such as aliphatic olefins, alicyclic olefins, aromatic vinyl compounds, dienes, vinyl ethers, silanes, vinylcarbazole, β-pinene, acenaphthylene and like monomers. For example, the block component (b) can be derived from a cation-polymerizable monomer such as:

aliphatic olefins (e.g., ethylene, propylene, 1-butene, 2-methyl-1-butene, 3-methyl-1-butene, pentene, hexane, 4-methyl-1-pentene and octene), alicyclic olefins (e.g., cyclohexene, vinylcyclohexane and norbornene);

aromatic vinyl monomers (e.g., styrene, o-, m- or p-methylstyrene, α-methylstyrene, β-methylstyrene, 2,6-dimethylstyrene, 2,4-dimethylstyrene, α-methyl-o-methylstyrene, α-methyl-m-methylstyrene, α-methyl-p-methylstyrene, β-methyl-o-methylstyrene, β-methyl-m-methylstyrene, β-methyl-p-methylstyrene, 2,4,6-trimethylstyrene, α-methyl-2,6-dimethylstyrene, α-methyl-2,4-dimethylstyrene, β-methyl-2,6-dimethylstyrene, β-methyl-2,4-dimethylstyrene, o-, m-, or p-chlorostyrene, 2,6-dichlorostyrene, 2,4-dichlorostyrene, α-chloro-o-chlorostyrene, α-chloro-m-chlorostyrene, α-chloro-p-chlorostyrene, β-chloro-o-chlorostyrene, β-chloro-m-chlorostyrene, β-chloro-p-chlorostyrene, 2,4,6-trichlorostyrene, α-chloro-2,6-dichlorostyrene, α-chloro-2,4-dichlorostyrene, β-chloro-2,6-dichlorostyrene, β-chloro-2,4-dichlorostyrene, o-, m-, or p-t-butylstyrene, o-, m-, or p-methoxystyrene, o-, m-, or p-chloromethylstyrene, o-, m-, or p-bromomethylstyrene, silyl-substituted styrene derivatives, indene, and vinyl naphthalene);

dienes (e.g., butadiene, isoprene, hexadiene, cyclopentadiene, cyclohexadiene, dicyclopentadiene, divinylbenzene, and ethylidenenorbornene);

vinyl ethers (e.g., ethers having a vinyl group as well as ethers having a substituted vinyl group such as propenyl group, including methylvinylether, ethylvinylether, (n- or iso)propylvinylether, (n-, sec-, tert-, or iso)butylvinylether, methylpropenylether, and ethylpropenylether);

silanes (e.g., vinyltrichlorosilane, vinylmethyldichlorosilane, vinyldimethylchlorosilane, vinyldimethylmethoxysilane, vinyltrimethylsilane, divinyldichlorosilane, divinyldimethoxysilane, divinyldimethylsilane, 1,3-divinyl-1,1,3,3-tetramethyldisiloxane, trivinylmethylsilane, γ-methacryloyloxypropyltrimethoxysilane, and γ-methacryloyloxypropylmethyldimethoxysilane);

vinylcarbazole;

β-pinene;

acenaphthylene; and like monomers.

These may be used singly or two or more of them may be used in combination. From the viewpoint of balanced physical properties and polymerization characteristics, among others, the use of aromatic vinyl monomers as the constituents is preferred.

The block structure of the isobutylene block copolymer of the polymer blend is not particularly restricted and thus can be a diblock copolymer, a triblock copolymer, a multiblock copolymer and the like having a straight chain, branched chain, star-shaped or other structure, or other block structures. The block structure of the isobutylene block copolymer of the polymer blend can provide for balanced physical properties and desired polymerization characteristics. Examples of block structures for the isobutylene block copolymer of the polymer blend include the following:

- a triblock copolymer composed of a block derived from an aromatic vinyl monomer (for example, a polystyrene block), a polymer block derived from isobutylene (for example, a polyisobutylene block), and a polymer block derived from the aromatic vinyl monomer (for example, a polystyrene block);
- a diblock copolymer composed of a polymer block derived from an aromatic vinyl monomer (for example, a polystyrene block) and a polymer block derived from isobutylene (for example, a polyisobutylene block); and
- a star-shaped block copolymer having at least three arms each composed of a polymer block derived from an aromatic vinyl monomer (for example, a polystyrene block) and a polymer block derived from isobutylene (for example, a polyisobutylene block).

It is possible to use these either singly or in combination of two or more species so that the desired physical properties and moldability/processability may be obtained. Among them, the triblock copolymers and diblock copolymers mentioned above are preferred, and poly(styrene-block-isobutylene-block-styrene triblock copolymer (SIBS) or poly(styrene-block-isobutylene) diblock copolymer (both of which include a polystyrene block as the aromatic vinyl monomer component and a polyisobutylene block as the isobutylene component) are more preferred.

The relative concentration of the block component (a) and the block component (b) as part of the isobutylene block copolymer of the polymer blend can be varied to provide for desired flexibility and physical properties. In the preferred embodiment, the mole fraction of the block component (b) as part of the isobutylene block copolymer is preferably between 15% and 45% (and more preferably between 25% and 35%), and the mole fraction of the block component (a) as part of the isobutylene block copolymer is preferably between 85% and 55% (and more preferably between 75% and 65%). Moreover, the Shore hardness of the isobutylene block copolymer of the polymer blend is preferably between 70A and 90A (and more particularly on the order of 80A).

The molecular weight of the isobutylene block copolymer of the polymer blend is not particularly restricted but, from the viewpoint of flowability, processability and physical properties, among others, the weight average molecular weight is preferably 30,000 to 500,000, more preferably 50,000 to 200,000, still more preferably 50,000 to 150,000. When the weight average molecular weight of the isobutylene block copolymer is lower than 30,000, there is a tendency toward tackiness (feel of tack) and the desired mechanical properties are not expressed to a sufficient extent. When, on the other hand, it exceeds 500,000, disadvantages will be experienced from the flowability and processability viewpoint.

The method of producing the isobutylene block copolymer of the polymer blend is not particularly restricted. In one example, the isobutylene block copolymer of the polymer blend is obtained by polymerizing a monomer component derived from isobutylene (which forms the block (a) components of the isobutylene block copolymer) and a monomer component derived from a monomer other than isobutylene (which forms the block (b) components of the isobutylene block copolymer) in the presence of a compound represented by the general formula:

$$(CR^1R^2X)_nR^3 \qquad (1)$$

In the above formula, X is a substituent selected from among halogen atoms and alkoxy or acyloxy groups containing 1 to 6 carbon atoms (preferably 1 to 3 carbon atoms). $R^1$ and $R^2$ are each independently is a hydrogen atom or a monovalent hydrocarbon group containing 1 to 6 carbon atoms (preferably 1 to 3 carbon atoms). $R^1$ and $R^2$ may be the same or different. $R^3$ is a mono- to hexavalent aromatic or alicyclic hydrocarbon group or a mono- to tetravalent aliphatic hydrocarbon group, and n represents a natural number of 1 to 6 when the $R^3$ group is an aromatic or alicyclic hydrocarbon group and, when the $R^3$ group is an aliphatic group, n represents a natural number of 1 to 4.

The compound represented by the formula (1) serves as an initiator and presumably forms a carbocation in the presence of a Lewis acid or the like, which serves as an initiation site for cationic polymerization. Among them, compounds wherein $R^3$ group in formula (1) is a mono- to trivalent aromatic hydrocarbon group are preferred.

During the polymerization of the isobutylene block copolymer, a Lewis acid catalyst may further be caused to coexist. Such Lewis acid catalyst may be any of those which can be used in cationic polymerization, including metal halides (such as $TiCl_4$, $TiBr_4$, $BCl_3$, $BF_3$, $BF_3.OEt_2$, $SnCl_4$, $SbCl_5$, $SbF_5$, $WCl_6$, $TaCl_5$, $VCl_5$, $FeCl_3$, $ZnBr_2$, $AlCl_3$ and $AlBr_3$), organometal halides (such as $Et_2AlCl$ and $EtAlCl_2$). The addition amount of the Lewis acid is not particularly restricted but can be selected according to the polymerization characteristics of the monomers employed and/or the polymerization concentration, among others. Generally, the Lewis acid can be used at amounts of 0.1 to 100 mole equivalents, preferably 1 to 50 mole equivalents, relative to 1 mole of the compound represented by the general formula (1).

In polymerizing the isobutylene block copolymer, an electron donor component may be used as desired. This electron donor component is considered to be effective in stabilizing the growing carbocations on the occasion of cationic polymerization and, when such an electron donor is added, a structurally controlled polymer with a narrow molecular weight distribution is formed. The electron donor component to be used is not particularly restricted but includes, for example, pyridines, amines, amides, sulfoxides, esters, and metal compound containing a metal atom-bound oxygen atom(s), among others.

The polymerization reaction for producing the isobutylene block copolymer can be carried out in an organic solvent. The organic solvent is not particular restricted provided that it will not essentially disturb the cationic polymerization. As specific example of the organic solvents, there may be mentioned, among others, halogenated hydrocarbons such as methyl chloride, dichloromethane, chloroform, ethyl chloride, dichloroethane, n-propyl chloride, n-butyl chloride and chlorobenzene; benzene and alkylbenzenes such as toluene, xylene, ethylbenzene, propylbenzene and butylbenzene; straight chain aliphatic hydrocarbons such as ethane, propane, butane, pentane, hexane, heptane, octane, nonane and decane; branched aliphatic hydrocarbons such as 2-methylpropane, 2-methylbutane, 2,3,3-trimethylpentane and 2,2,5-trimethylhexane; cyclic aliphatic hydrocarbons such as cyclohexane, methylcyclohexane and ethylcyclohexane; and paraffin oils derived from petroleum fractions by purification by hydrogenation.

The polymerization reaction for producing the isobutylene block copolymer is preferably carried out in a controlled temperature range between −100° C. and 0° C. (most preferably in a range between −80° C. and −30° C.).

These relative concentrations of the isobutylene block copolymer and the thermoplastic polyurethane material of the polymer blend can be adjusted to control the tensile strength and degree of hydrophobicity of the polymer blend. The mole fraction of the isobutylene block copolymer as part of the polymer blend can range from 1% to 50%. In the preferred embodiment, the mole fraction of the isobutylene block copolymer of the polymer blend is in the range of 2% to 15% (and more preferably on the order of 10%), and the mole fraction of the thermoplastic polyurethane material of the polymer blend is in the range of 98% to 85% (and more preferably on the order of 90%). The polymer blend can have a maximum tensile strength in the range between 20 and 40 MPa (more preferably in the range between 25 MPa and 35 MPa). The maximum tensile strength of the polymer blend is the maximum stress on the stress-strain curve, which can be measured by subjecting a sample of the polymer blend to pull testing in a tension tester (for example, a tension tester sold commercially by Instron Corp. of Norwood, Mass.). In the preferred embodiment, the hardness of the polymer blend can be characterized by a Shore hardness in a range between 70A and 80A. Shore hardness is measured by a Shore durometer (for example, a Shore durometer sold commercially by Instron Corp. of Norwood, Mass.), which typically includes a diamond-tipped hammer that is allowed to fall from a known height onto the test specimen. The hardness number depends on the height to which the hammer rebounds; the harder the material, the higher the rebound. In the preferred embodiment, the elastic characteristics of the isobutylene block copolymer and the thermoplastic polyurethane material of the polymer blend are similar so as to provide a smooth stress/strain curve. Moreover, if blended by melt processing, the melting points of the isobutylene block copolymer and the thermoplastic polyurethane material of the blend are in the same range to avoid one polymer burning before the other is melted.

In addition, some polyurethanes demonstrate better compatibility with isobutylene block copolymer than others. For example, polyether urethane using MDI as the diisocyanate, polytetramethylene glycol as the macroglycol and 1,4-butanediol as the chain extender when blended with SIBS of 20 mole percent styrene, provides a clear transparent polymer. On the other hand, a polycarbonate urethane comprised of MDI, poly(tetramethylene carbonate)glycol and 1.4-butanediol bended with SIBS provides a white opaque polymer. Therefore, for certain applications where transparency is required the aromatic polyether urethane is preferred. Compatibilizers such as polyisobutylene capped with polyurethane groups can also be added to the blend to help render the SIBS more compatible with the polyurethane.

Other polymeric components and/or additives can be included in the polymer blend. The additives can include lubricants, antioxidants, UV stabilizers, melt processing aids, extrusion processing aids, blocking agents, pigments, radioopaques, fillers and the like. The lubricants can be fatty acid type lubricants, paraffin type lubricants or combination thereof. The fatty acid type lubricants can include a fatty acid metal salt type lubricant, a fatty acid amide type lubricant, a fatty acid ester type lubricant, an aliphatic alcohol type lubricant, a fatty acid-polyhydric alcohol partial ester and/or combinations thereof. The paraffin type lubricant can include a paraffin wax, a liquid paraffin, a polyethylene wax, an oxidized polyethylene wax, a polypropylene wax and/or combinations thereof.

Blending of the isobutylene block copolymer and the thermoplastic polyurethane material can be performed by mixing together the polymers in a melt or by mixing the polymers in solution. Melt blending can be carried out in a hot mixing machine such as a single-screw extruder, twin-screw extruder, Brandbury mixer, Brabender mixer, or a high-shear mixer. Both polymers are heated together until sufficiently soft to allow mixing, which is preferably accomplished at temperature between 150° C. and 200° C. Blending in solution can be carried out is a suitable solvent. For example, most isobutylene block copolymers and thermoplastic polyurethane materials are soluble in tretrahydrofuran (THF). Therefore, for example purposes only, a 15% solution of polyether urethane in THF can be mixed with a 15% solution of SIBS. The solvent can then be flashed off or the polymer can be precipitated from solution by the addition of copious amounts of isopropyl alcohol. The polymer blend so formed can be pelletized and processed for use as the outer insulating part 15 and the inner insulating part 17 of the lead body as described herein.

The biocompatibility of the insulating structures 15/17 can be improved by forming a biocompatible coating layer 21 on the outer surface of the outer insulating part 15 as shown in FIG. 1B. In one embodiment, both the outer insulating part 15 and coating layer 21 are realized from SIBS. The coating layer 21 of SIBS can be formed on the outer insulating part 15 by dip coating the outer insulating part 15 (possibly with the flexible conductor element(s) 13 wound about the inner insulating part 17 and encapsulated by the outer insulating part 17) in a dipping solution of SIBS dissolved in a non-polar solvent. In one example, the dipping solution includes 0-15% SIBS by weight (more preferably 2-6% SIBS by weight). The non-polar solvent can be hexane, toluene, methyl cyclohexane, etc. While the outer insulating part 15 is submerged in the dipping solution, the SIBS from the polymer blend of the outer insulating part 15 becomes slightly solubilized and interpenetrates with a SIBS coating layer laid down from the dipping solution, resulting in a very strong solvent bond of the SIBS coating layer to the outer insulating part 15. These constructs are strong and do not risk delaminating as would a surface coating of SIBS onto pure polyurethane. Alternatively, the coating layer 21 of SIBS can be formed by dipping the outer insulating part 15 (possibly with the flexible conductor element(s) 13 wound about the inner insulating part 17 and encapsulated by the outer insulating part 17) in a solvent that causes the SIBS component in the polymer blend of the outer insulating part 17 to migrate and coat the outer surface of the outer insulating part 17. This outer surface can be wiped with a cloth containing solvent only which will smear the migrated SIBS over the outer surface of the outer insulating part 17 to form the coating layer 21 of SIBS.

Importantly, the polymer blend of the outer insulating part 15 and the inner insulating part 17 of the lead body is less permeable to oxygen relative to polyurethane alone due to the oxygen permeability characteristics of the isobutylene block copolymer of the blend. The measure of oxygen permeability of a material is in non-SI units called "Barrers" or "Barrer number." These units were defined by (and are important to the contact lens industry) because the supply of oxygen to the cornea is mandatory for survival of the cornea and the comfort of the wearer. Most polymers have a Barrer number of approximately 25 to 35. Polyurethane has a Barrer number in the range of 25-30. The polymer blend of the present disclosure has a Barrer number in the range of 15-25. The reduced oxygen permeability characteristics of the polymer blend as part of both the outer insulating structure 15 and the inner insulating structure 17 of the lead body thus limits oxygen flow through the insulating structures to the metal conductor from inside (i.e., from the inside channel) and from outside the lead body and thus provides improved resistance to MIO and ESC while maintaining the flexibility and desired tensile strength of the insulating structure (parts 15, 17) of the lead body.

The inner insulating part 17 can be formed by dip coating, spraying or co-extrusion over a core. The flexible conductor element(s) 13 can be wound about the inner insulating part 17. The outer insulating part 15 can be formed by dip coating, spraying or co-extrusion over the resultant structure. The core can then be removed to provide the lead body as shown. Details of exemplary processing for producing this structure is set forth in U.S. Pat. No. 4,484,586 to McMikle et al., herein incorporated by reference in its entirety.

In another embodiment, the inner insulating part 17 of the lead body of FIG. 1B is formed from a thermoplastic polyurethane material as described herein, the outer insulating part 15 of the lead body of FIG. 1B is formed from a compatibilizer polymer, and the outer coating layer 21 of the lead body of FIG. 1B is formed from an isobutylene block copolymer as described herein. The compatibilizer polymer of the outer insulating part 15 is compatible with both the thermoplastic polyurethane material of the inner insulating part 17 and the isobutylene block copolymer of the outer coating layer 21 in that it readily bonds to both these materials while avoiding interfacial delamination and disbonding over time. The compatibilizer polymer of the outer insulating part 15 can be a polymer blend of a thermoplastic polyurethane material and an isobutylene block copolymer as described herein. In one example, the thermoplastic polyurethane material of the inner insulating part 17 is a polyether urethane (such as Pellethane® 80A from the Lubrizol Corporation of Wickliffe, Ohio), the isobutylene block copolymer of the outer coating layer 21 is a SIBS polymer, and the compatibilizer polymer of the outer insulating part 15 is a polymer blend of the polyether urethane of the inner insulating part 15 and the SIBS polymer of the outer coating layer 21.

In this embodiment, the inner insulating part 17 can be formed by dip coating, spraying or co-extrusion of the thermoplastic polyurethane material over a core. The flexible conductor element(s) 13 can be wound about the inner insulating part 17. The outer insulating part 15 can be formed by dip coating, spraying or co-extrusion of the compatibilizer polymer over the resultant structure. The coating layer 21 can be formed by dip coating, spraying or co-extrusion of the isobutylene block copolymer on the resultant structure. The core can then be removed to provide the lead body as shown.

For the case where the outer coating layer 21 is SIBS, the outer coating layer 21 can be formed on the outer insulating part 15 by dip coating the structure in a dipping solution of SIBS dissolved in a non-polar solvent. In one example, the dipping solution includes 0-15% SIBS by weight (more preferably 2-6% SIBS by weight). The non-polar solvent can be hexane, toluene, methyl cyclohexane, etc. While the outer insulating part 15 is submerged in the dipping solution, the SIBS from the polymer blend of the outer insulating part 15 becomes slightly solubilized and interpenetrates with a SIBS coating layer laid down from the dipping solution, resulting in a very strong solvent bond of the SIBS coating layer to the outer insulating part 15. Alternatively, the outer coating layer 21 of SIBS can be formed on the outer insulating part 15 by dipping the structure in a solvent that causes the SIBS component in the polymer blend of the outer insulating part 17 to migrate and coat the outer surface of the outer insulating part 17. This outer surface can be wiped with a cloth containing solvent only which will smear the migrated SIBS over the outer surface of the outer insulating part 17 to form the outer coating layer 21 of SIBS.

Figure 1C:
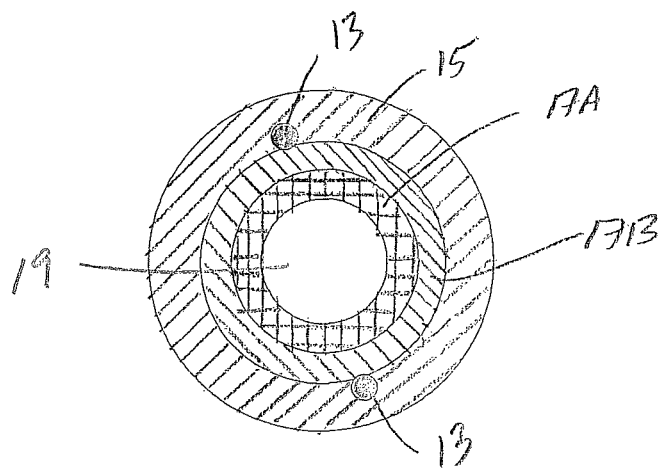
FIG. 1C is a cross-sectional view of another embodiment of a pacemaker lead body in accordance with the present application.

In yet another embodiment shown in FIG. 1C, the inner insulating part 17 of the lead body is defined by a multi-layer structure including an inner layer 17A formed from a thermoplastic polyurethane material as described herein and an outer layer 17B formed from a compatibilizer polymer. The outer insulating part 15 of the lead body of FIG. 1C is formed from an isobutylene block copolymer as described herein. The compatibilizer polymer of the layer 17B is compatible with both the thermoplastic polyurethane material of the inner layer 17A and the isobutylene block copolymer of the outer insulating part 15 in that it readily bonds to both these materials while avoiding interfacial delamination and disbonding over time. The compatibilizer polymer of layer 17B can be a polymer blend of a thermoplastic polyurethane material and an isobutylene block copolymer as described herein. In one example, the thermoplastic polyurethane material of layer 17A is a polyether urethane (such as Pellethane® 80A from Lubrizol Corporation of Wickliffe, Ohio), the isobutylene block copolymer of the outer insulating part 15 is a SIBS polymer, and the compatibilizer polymer of layer 17B is a polymer blend of the polyether urethane of layer 17A and the SIBS polymer of the outer insulating part 15.

In this embodiment, the multi-layer structure of layers 17A, 17B of the inner insulating part 17 can be formed by dip coating, spraying or co-extrusion of the thermoplastic polyurethane material of layer 17A over a core followed by dip coating, spraying or co-extrusion of the compatibilizer polymer of layer 17B over the resultant structure. The flexible conductor element(s) 13 can be wound about the multi-layer structure of layers 17A, 17B of the inner insulating part 17. The outer insulating part 15 can be formed by dip coating, spraying or co-extrusion of the isobutylene block copolymer on the resultant structure. The core can then be removed to provide the lead body as shown.

For the case where the outer insulating part 15 is SIBS, the outer insulating part 15 can be formed by dip coating the structure in a dipping solution of SIBS dissolved in a non-polar solvent. In one example, the dipping solution includes 0-15% SIBS by weight (more preferably 2-6% SIBS by weight). The non-polar solvent can be hexane, toluene, methyl cyclohexane, etc. While the structure is submerged in the SIB dipping solution, the SIBS from the compatibilizer polymer of the layer 17B becomes slightly solubilized and interpenetrates with the SIBS layer laid down from the dipping solution, resulting in a very strong solvent bond of the SIBS layer (the outer insulating part 15) to layer 17B.

Figure 1D:
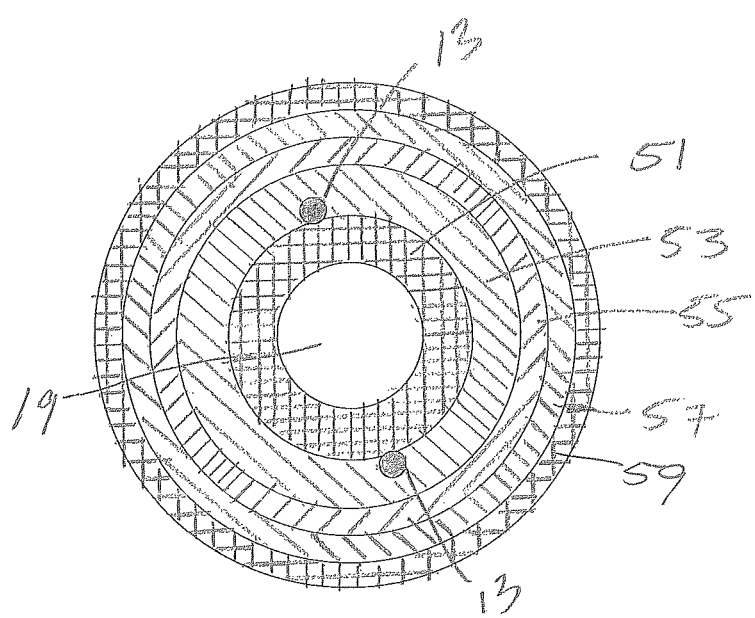
FIG. 1D is a cross-sectional view of yet another embodiment of a pacemaker lead body in accordance with the present application.

In yet another embodiment shown in FIG. 1D, the lead body is defined by a multi-layer structure including an inner layer 51, a first intermediate layer 53 that covers the inner layer 51, a second intermediate layer 55 that covers layer 53, a third intermediate layer 57 that covers layer 55, and an outer layer 59 that covers layer 57. The inner layer 51 is formed from an isobutylene block copolymer as described herein. The first intermediate layer 53 is formed from a compatibilizer polymer. The second intermediate later 55 is formed from a thermoplastic polyurethane material as described herein. The compatibilizer polymer of the first intermediate layer 53 is compatible with both the isobutylene block copolymer of the inner layer 51 and the thermoplastic polyurethane material of the second intermediate layer 55 and in that it readily bonds to both these materials while avoiding interfacial delamination and disbonding over time. The compatibilizer polymer of layer 53 can be a polymer blend of a thermoplastic polyurethane material and an isobutylene block copolymer as described herein. The third intermediate layer 57 is formed from a compatibilizer polymer. The outer layer 59 is formed from an isobutylene block copolymer as described herein. The compatibilizer polymer of the third intermediate layer 57 is compatible with both the thermoplastic polyurethane material of the second intermediate layer 55 and the isobutylene block copolymer of the outer layer 59 and in that it readily bonds to both these materials while avoiding interfacial delamination and disbonding over time. The compatibilizer polymer of layer 57 can be a polymer blend of a thermoplastic polyurethane material and an isobutylene block copolymer as described herein.

In one example, the isobutylene block copolymer of the inner layer 51 and the outer layer 59 is a SIBS polymer, the thermoplastic polyurethane material of the second intermediate layer 55 is a polyether urethane (such as Pellethane® 80A from Lubrizol Corporation of Wickliffe, Ohio), and the compatibilizer polymer of the first intermediate layer 53 and the third intermediate layer 57 is a polymer blend of the polyether urethane of layer 55 and the SIBS polymer of the inner and outer layers 51, 59.

In this embodiment, the multi-layer structure of layers 51, 53, 55, 57 and 59 can be formed by dip coating, spraying or co-extrusion of the isobutylene block copolymer over a core to define the inner layer 51. The flexible conductor element(s) 13 can be wound about the inner layer 51 (and/or possibly wound about one or more of the intermediate layers 53, 55, and 57). The compatibilizer polymer of the first intermediate layer 53 can be formed by dip coating, spraying or co-extrusion of the compatibilizer polymer over the resultant structure. The thermoplastic polyurethane material of the second intermediate layer 55 can be formed by dip coating, spraying or co-extrusion of the isobutylene block copolymer over the resultant structure. The compatibilizer polymer of the third intermediate layer 57 can be formed by dip coating, spraying or co-extrusion of the compatibilizer polymer over the resultant structure. The isobutylene block copolymer of the outer layer 59 can be formed by dip coating, spraying or co-extrusion of the isobutylene block copolymer over the resultant structure. The core can then be removed to provide the lead body as shown.

For the case where the outer layer 59 is SIBS, the outer layer 59 can be formed by dip coating the structure in a dipping solution of SIBS dissolved in a non-polar solvent. In one example, the dipping solution includes 0-15% SIBS by weight (more preferably 2-6% SIBS by weight). The non-polar solvent can be hexane, toluene, methyl cyclohexane, etc. While the structure is submerged in the SIB dipping solution, the SIBS from the compatibilizer polymer of the third intermediate layer 57 becomes slightly solubilized and interpenetrates with the SIBS layer laid down from the dipping solution, resulting in a very strong solvent bond of the SIBS outer layer 59 to the third intermediate layer 57. Similarly, for the case where the inner layer 51 is SIBS, the SIBS from the compatibilizer polymer of the first intermediate layer 53 can become slightly solubilized and interpenetrate with the SIBS inner layer 51, resulting in a very strong solvent bond of the SIBS inner layer 51 to the first intermediate layer 53.

There have been described and illustrated herein several embodiments of an improved pacemaker lead body and methods of constructing same. While particular embodiments have been described, it is not intended that the claims be limited thereto, as it is intended that the claims be as broad in scope as the art will allow and that the specification be read likewise. Thus, while particular constituent elements have been disclosed for the isobutylene block copolymer of the blend, it will be appreciated that other isobutylene derived constituents can be used as well. For example, in an alternate embodiment, polyisobutylene of molecular weight greater than 1,000 Daltons can be used as a substitute for the isobutylene block copolymer of the blend. In addition, while particular configurations of the pacemaker lead body have been disclosed, it will be understood that the polymer blend of the present disclosure can be used in other configurations. For example, and not by way of limitation, it is contemplated that the inner insulating part can be omitted and/or formed as a solid core and/or formed from a different polymer material. In yet other embodiments, multi-axial configurations can be provided where multiple flexible conductors are concentrically spaced apart radially from one another between insulating structures. An example of such a structure is illustrated in FIG. 2 of U.S. Pat. No. 7,555,349, herein incorporated by reference in its entirety. In another embodiment, configurations can be provided where multiple flexible conductors are non-concentrically spaced apart and protected by surrounding insulating structure(s). Examples of such configurations are disclosed in U.S. Pat. No. 5,545,203 and U.S. Pat. No. 5,584,873, herein incorporated by reference in their entireties. Moreover, while particular applications have been disclosed in reference to implantable medical devices for electrical stimulation, it will be appreciated that the embodiments of the implantable lead structures as described herein can be used for other implantable medical device applications, such as electrical sensing applications. Furthermore, the polymeric materials of the implantable lead structures as described herein can be used for other medical implant applications, such as for at least a part of an artificial disk for the spine, a dynamic stabilizer for the spine, an artificial tendon, an artificial ligament, an indwelling catheter, a drug delivery device, a hernia mesh, a heart valve, or other implantable medical device. It will therefore be appreciated by those skilled in the art that yet other modifications could be made to the provided disclosure without deviating from its spirit and scope as claimed.

I claim:

1. An implantable medical device for electrical stimulation or sensing, the medical device comprising:
   a body supporting at least one flexible elongate conductor element, wherein the body includes an insulating structure that protects the conductor element, wherein the insulating structure includes at least a first polymer layer, a second polymer layer and a third polymer layer;
   wherein the second polymer layer is disposed between the first polymer layer and the third polymer layer and covers the first polymer layer and interfaces to both the first polymer layer and the third polymer layer;
   wherein the third polymer layer covers and interfaces to the second polymer layer;
   wherein the first polymer layer is formed from a thermoplastic polyurethane material;
   wherein the third polymer layer is formed from an isobutylene block copolymer; and
   wherein the second polymer layer is formed from a polymer blend of the thermoplastic polyurethane material of the first polymer layer and the isobutylene block copolymer of the third polymer layer.

2. A medical device according to claim 1, wherein: the isobutylene block copolymer of the third polymer layer and of the polymer blend of the second polymer layer has a block derived from isobutylene and a block derived from a monomer component other than isobutylene.

3. A medical device according to claim 2, wherein: the monomer component other than isobutylene is a cation-polymerizable monomer.

4. A medical device according to claim 3, wherein: the cation-polymerizable monomer is selected from the group consisting of aliphatic olefins, alicyclic olefins, aromatic vinyl compounds, dienes, vinyl ethers, silanes, vinylcarbazole, β-pinene, and acenaphthylene.

5. A medical device according to claim 2, wherein: the monomer component other than isobutylene is a vinyl aromatic monomer.

6. A medical device according to claim 2, wherein: the monomer component other than isobutylene comprises styrene.

7. A medical device according to claim 1, wherein: the isobutylene block copolymer of the third polymer layer and of the polymer blend of the second polymer layer comprises a block of polyisobutylene and a block of polystyrene.

8. A medical device according to claim 1, wherein: the isobutylene block copolymer of the third polymer layer and of the polymer blend of the second polymer layer is a triblock copolymer comprising a block of polystyrene, a block of polyisobutylene and a block of polystyrene.

9. A medical device according to claim 1, wherein: the third polymer layer is an outer coating layer.

10. A medical device according to claim 1, wherein: the insulating structure encapsulates the conductor element.

11. A medical device according to claim 1, wherein: the conductor element includes a coiled wire conductor defining a central axis with an outer surface facing radially outward away from the central axis and an inner surface facing radially inward toward the central axis.

12. A medical device according to claim 1, wherein: the polymer blend of the second polymer layer is mixed in a melt or in a solution.

13. A medical device according to claim 1, wherein: the first polymer layer defines a guide channel lumen.

14. A medical device according to claim 13, wherein: the conductor element is encapsulated by the third polymer layer.

15. A medical device according to claim 1, further comprising:
an inner polymer layer that defines a guide channel lumen; and
an intermediate polymer layer that is disposed between the inner polymer layer and the first polymer layer and covers the inner polymer layer and interfaces to both the inner polymer layer and the first polymer layer.

16. A medical device according to claim 15, wherein: the inner polymer layer is formed from an isobutylene block copolymer; and
the intermediate polymer layer is formed from a polymer blend of the thermoplastic polyurethane material of the first polymer layer and the isobutylene block copolymer of the inner polymer layer.

17. A medical device according to claim 15, wherein: the conductor element is encapsulated by the intermediate polymer layer.

* * * * *